(12) United States Patent
Vose et al.

(10) Patent No.: US 7,903,243 B2
(45) Date of Patent: Mar. 8, 2011

(54) AUTOMATIC BREWSTER ANGLE REFRACTOMETER

(76) Inventors: James Arnold Vose, Lincoln, ME (US); James Patrick McClymer, Orono, ME (US); Thomas Woodrow Tripp, Jr., Brewer, ME (US)

(*) Notice: Subject to any disclaimer, the term of this patent is extended or adjusted under 35 U.S.C. 154(b) by 0 days.

(21) Appl. No.: 12/622,255

(22) Filed: Nov. 19, 2009

(65) Prior Publication Data
US 2010/0128267 A1  May 27, 2010

Related U.S. Application Data

(60) Provisional application No. 61/199,866, filed on Nov. 21, 2008.

(51) Int. Cl.
*G01N 21/41* (2006.01)
(52) U.S. Cl. ........................................ 356/128; 356/131
(58) Field of Classification Search ........... 356/121–137
See application file for complete search history.

(56) References Cited

U.S. PATENT DOCUMENTS

| 2,885,923 | A | * | 5/1959 | Simmons | 356/136 |
|---|---|---|---|---|---|
| 3,975,097 | A | | 8/1976 | Minto | |
| 4,692,024 | A | * | 9/1987 | Bloss | 356/135 |
| 5,048,970 | A | * | 9/1991 | Milosevic et al. | 356/445 |
| 5,572,314 | A | | 11/1996 | Hyman, Jr. et al. | |

* cited by examiner

*Primary Examiner* — Gregory J Toatley
*Assistant Examiner* — Jarreas C Underwood
(74) *Attorney, Agent, or Firm* — Anthony D. Pellegrini, Esquire

(57) ABSTRACT

An improved refractometer for automatically determining the refractive index of a test subject by using principles embodied in Brewster's Angle, the refractometer comprising a light source, a light detector, a subject mount for securing the test subject to the device, a positioning device to orient the light source and light detector to the subject such that the angles of the light source and light detector to the subject are substantially identical, a data gathering device to automatically retrieve relevant data regarding the angles of the light source and light detector to the subject and the light intensity of the reflected light, and a computational device to process the data using algorithms taking into account the principles embodied in Brewster's Angle and/or Fresnel Equations in order to arrive at the refractive index of the test subject.

21 Claims, 7 Drawing Sheets

AUTOMATIC BREWSTER ANGLE REFRACTOMETER

CROSS REFERENCE TO RELATED APPLICATION

This application claims priority to a provisional application, U.S. Ser. No. 61/199,866, filed Nov. 21, 2008, by Vose, James A., McClymer, James P., and Tripp, Thomas W., which is hereby incorporated by reference.

BACKGROUND OF THE INVENTION

1. Technical Field

The invention relates generally to the field of materials analysis, and in particular to the analysis of minerals and gemstones. More specifically, the invention is directed to an improved high-speed device for the automated measurement of the real part of the refractive index of a substance.

2. Description of Prior Art

It is well known in the art that the identity of gemstones and other minerals may be determined by their indices of refraction. The refractive indices for gemstones range from about 1.4 to 2.8. The refractive indices for other minerals fall within a greater range. Standard tables are provided equating a given index of refraction with a given substance.

Current common methods of identifying substances by their refractive indices, primarily utilizing critical angle refractometry (CAR), are incapable of measuring refractive index beyond 1.81, and thus not useful in identifying many useful and economically valuable gems and minerals. This is because CAR requires the use of a liquid medium into which the subject substance is placed. The liquid medium has a known refractive index, which must be higher than the refractive index of the test substance. The liquids providing the most accurate measurements, such as a solution of tetraiodo-ethylene and sulfur in methylene iodide, have a refractive index of only 1.81, representing the upper limit of substances that can be tested using CAR. However, this upper limit is below the refractive index of diamond (2.42) and of most diamond imitations, which range from 1.95 (for zircon) to 2.65 or more (for rutile), and thus CAR cannot distinguish between true and imitation diamonds. Moreover, these liquids are extremely toxic and corrosive.

In addition, most CAR refractometers rely on room light and produce a fuzzy reading reducing the accuracy of the measurement. Even when a monochromatic (usually sodium) light source is used the width of the resulting line viewed through the refractometer increases the uncertainty of the measurement. Thus, current methods produce low accuracy measurements and rely on operator skills for manipulation and interpretation.

Notwithstanding these limitations, CAR refractometers are by far the most commonly available and used devices to measure refractive indices by gemologists.

While the prior art discloses various attempts to eliminate the use of liquid refractory media, such as Minto, U.S. Pat. No. 3,975,097, Bloss, U.S. Pat. No. 4,692,024, and Hyman, Jr., et al., U.S. Pat. No. 5,572,314, none of the disclosed prior art offers all of the functionality disclosed in the present invention. Moreover, the implementation of similar individual concepts in earlier patents differs significantly with the implementation of the present invention. Thus none of the disclosed prior art anticipates the present invention.

It is thus an objective of the present invention to provide an improved refractometer that aids in the automatic identification of gems and minerals by measuring the refractive index thereof.

It is a further objective of the present invention to provide an improved refractometer that calculates the refractive index of a substance without the use of toxic and/or corrosive liquids such as methylene iodide.

It is a further objective of the present invention to provide an improved refractometer that can measure a range of refractive indices from at least 1.300 to 3.000.

It is a further objective of the present invention to provide an improved refractometer having greater accuracy than prior devices.

It is a further objective of the present invention to provide an improved refractometer that requires less operator skill than prior devices and reduces errors due to operator error.

Other objectives of the present invention will be readily apparent from the description that follows.

SUMMARY OF THE INVENTION

Refractive index measurement is a key test in gemstone identification. While the focus of the present invention is development of a tool for the gemological industry, refractive index measurements are important in many different industrial processes, research and science, and technology education. The device of the present invention is capable of measuring a refractive index in the range from at least 1.300 to 3.000 with precision to at least the third decimal place.

The device of the present invention uses custom designed software for instrument control, data acquisition, analysis, and presentation as part of a precision measuring instrument with multiple applications in industry.

The index of refraction of a substance is a measure of how much the speed of light is reduced inside the substance. For example, ordinary glass has a refractive index close to 1.5, which means that in glass, light travels at 1/1.5 or about ⅔ the speed of light in a vacuum. Because different substances have different indices of refraction, determining the index of refraction of an unknown substance can be used to identify that substance by comparing the calculated index of refraction against a table of values for known substances.

Brewster's Angle (also known as the polarization angle), named after the Scottish physicist Sir David Brewster (1781-1868), is an angle of incidence at which light with a particular polarization is perfectly transmitted through a surface of a substance, with no reflection (i.e., polarized light directed onto a planar surface of a substance at the Brewster's Angle for that substance will not reflect from that surface). Specifically, Brewster's Angle is the angle at which unpolarized light (consisting of a mixture of electric field vibrations perpendicular (S-polarization) and parallel (P-polarization) to the plane of incidence) minimally reflects the P-polarized wave. In the case of no absorbance, no P-polarized light is reflected. Thus, measurement of minimum of P-polarized light is used to determine Brewster's Angle which is used to calculate the refractive index of the scattering material relative to air (the medium the light was in before scattering from the material). The tangent of this angle equals the refractive index of the reflecting material relative to air.

Using a measured Brewster's Angle allows for the solving of a formula for the index of refraction of a substance. Thus, a device that employs the principles embodied by Brewster's Angle can be used to determine the refractive index of an unknown substance for the purpose of identifying that substance by its refractive index. An obvious application of such a device would be to determine the composition of unknown gemstones. Gemstones, having relatively smooth, planar facets, are particularly good substances for calculating the index of refraction to a high degree of accuracy.

While the present invention uses the principles embodied in Brewster's Angle in determining the index of refraction of a substance, it does not actually calculate Brewster's Angle for that substance. The inherent "noise" in reflected light makes determining Brewster's Angle from direct observation extremely difficult. Instead, the present invention gathers data involving angles of incidence of light waves and the intensity of the resulting reflected light waves to create a curve of measured data points, and then creates an equation that best fits the curve. The equation is then solved for the index of refraction.

The function used to fit to the measured data to the equation to determine the index of refraction (which is typically designated by the letter "n") involves a non-linear least squares method. Other methods could potentially be used as well. The function consists of the Fresnel Equations for S and P reflected light intensity. (The Fresnel Equations describe the behavior of light when moving between media of differing refractive indices.) The intensity from both the S and P polarized light are added together with a weight determined by a parameter (designated "A") which ranges from 0 to 1. Parameter A is applied to the Fresnel Equation for S and Parameter 1-A is applied to the Fresnel Equation for P. Parameter A is a calibration constant which is determined in advance for a particular device, determined by the polarizer orientation and efficiency of that device. In the case of A=1, at the Brewster's Angle the intensity is 0 (except for background signal and noise). However, A=1 requires perfect alignment and perfect polarizers. In practice Parameter A is defined to be something less than 1, typically in the range 0.85 to 0.95, and preferably approximately 0.9. This results in the function weighting substantially in favor of the Fresnel Equation for S, but still taking into account some small contribution by the Fresnel Equation for P. A constant designated "C" is added to account for background "noise" such as stray light, and an overall scale factor "s" is used to control for the brightness of the light source and the efficiency of the light detector and collection optics.

In addition to the above defined constants, the value I is the measured intensity of the reflected light and the value theta is the calculated angle of the reflected light. From observed measurements of I over multiple different angles theta, the index of refraction n can be solved.

The function itself is as follows:

$$I = s*(A*(n^2*\cos(theta)-\sqrt{n^2-\sin(theta)^2}))^2 /$$
$$(n^2*\cos(theta) + \sqrt{n^2-\sin(theta)^2}))^2 +$$
$$(1-A)*(\cos(theta)-\sqrt{n^2-\sin(theta)^2}))^2 /$$
$$(\cos(theta) + \sqrt{n^2-\sin(theta)^2})^2) + C$$

The present invention requires a constant intensity light source, a light detector which can measure the intensity of light waves falling thereupon, and a means for adjusting the angles of the light source and the light detector to the subject, as well as a means for capturing data involving the angles and light intensity and means of applying that data to the above-described formulas.

In the preferred embodiment the light source is a yellow light emitting diode, with collimating lens and a polarizing element, having a peak wavelength at 589 nm so that measurements of the refractive index can easily be compared with tabulated data for gems and minerals which are predominately measured using the Sodium D line at 589 nm. Use of a wavelength near this value makes the measurements of refractive index easy to compare with standard values for identification. In an alternative embodiment multiple light sources are used so that dispersion can be measured by measuring the index of refraction for more than one wavelength of light. Dispersion is the difference in the indices of refraction of the different wavelengths. Measuring the dispersion of different light waves is a common identification tool used in the industry for identifying a substance. The two light sources at different wavelengths that are most commonly used are near the B and G Fraunhoffer lines (687.7 nm and 430.8 nm respectively). The difference in the refractive indices of substances using these two wavelengths is set forth in standard tables. In addition, multiple refractive index readings can be averaged and standard deviations can be measured, as well as other relevant statistical information. In an alternative embodiment the polarizing element could be incorporated into the light detector rather than the light source.

To obtain a useful data set, the present invention comprises a positioning device capable of positioning the light source and the light detector relative to the test subject, such that the angle theta of the orientation of the light source to the subject is identical to the angle theta of the orientation of the light detector to the subject. As the light source and the light detector are positioned through various angles relative to the subject, the intensity of the reflected light falling upon the light detector is measured. A computing device uses the data to calculate the refractive index of the test subject by use of a curve fitting algorithm to extract the index of refraction from the data set of reflectivity as a function of angle. In the preferred embodiment a computer-controlled pantograph is used to orient the light source and the light detector relative to the test subject.

Other features and advantages of the present invention are described below.

DETAILED DESCRIPTION OF THE INVENTION

Figure 1:
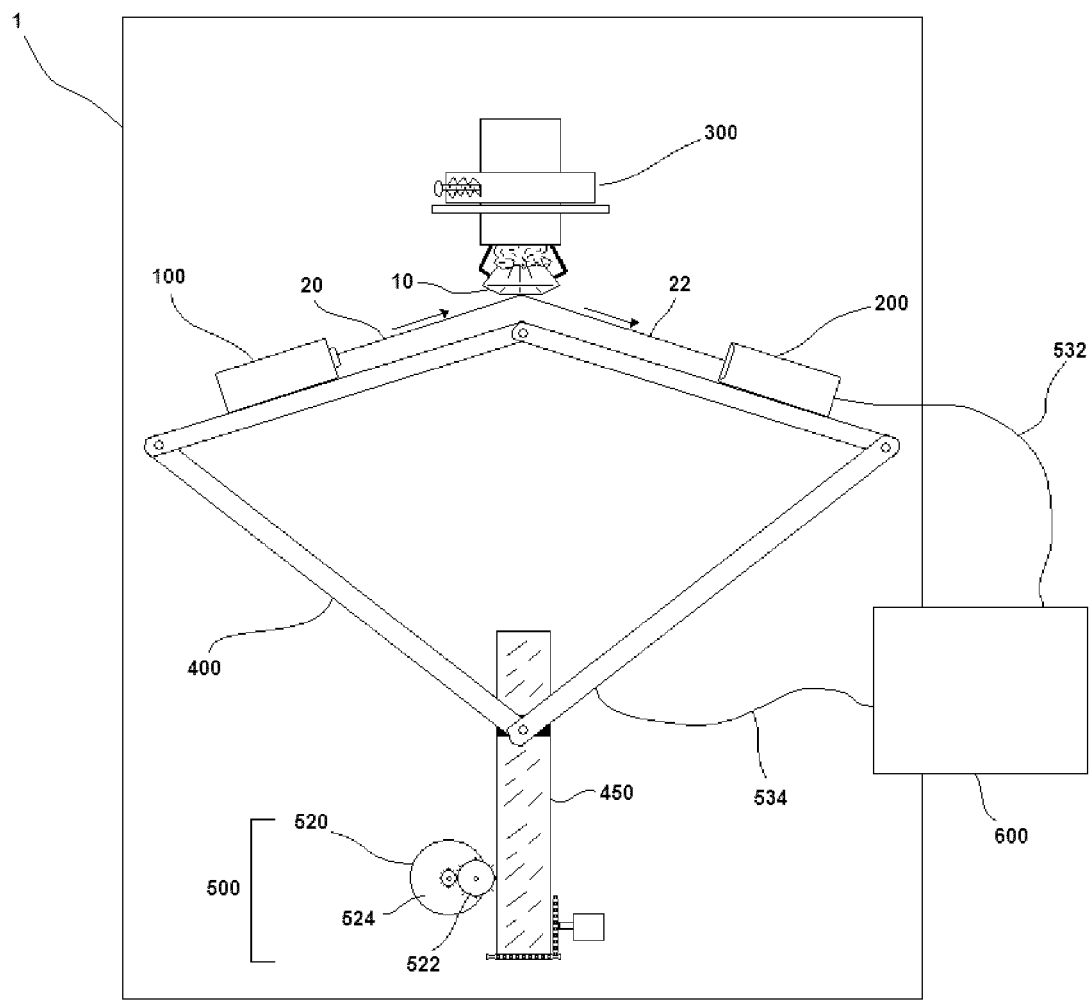
FIG. 1 depicts a schematic front plan view of one embodiment of the refractometer, showing the light source, the light detector, the subject mount, the positioning device, the data gathering device, and the computational device.

An aspect of the present invention discloses an improved refractometer 1 for automatically determining the refractive index of a test subject 10. The refractometer 1 minimally comprises a light source 100, a light detector 200, a subject mount 300 for securing the test subject 10 to the device, a polarizer 104, a positioning device 400 to orient the light source 100 and light detector 200 to the subject 10, a data gathering device 500 to automatically retrieve relevant data, and a computational device 600 to process the data using algorithms taking into account the principles embodied in Brewster's Angle and/or Fresnel Equations in order to arrive at the refractive index of the test subject 10. See FIG. 1. In an alternative embodiment of the present invention the refractometer 1 further comprises a filter to make the light waves more monochromatic.

The light source 100 can be any device known in the art capable of emitting light waves 20 at a substantially constant intensity. In the preferred embodiment the light waves 20 should be of a known spectrum, and in the most preferred embodiment the light waves 20 should be consistent with the standards used in the gemological industry for consistent application of calculated refractive indices against known standards. To that end, the light source 100 should be a yellow light emitting diode 102 capable of emitting light waves 20 falling within the range of 550 nm to 600 nm, and most preferably having a peak wavelength at 589 nm, consistent with the wavelength of a sodium lamp. However, other wavelengths of light can also be used, including multi-spectrum and natural light.

Figure 4:
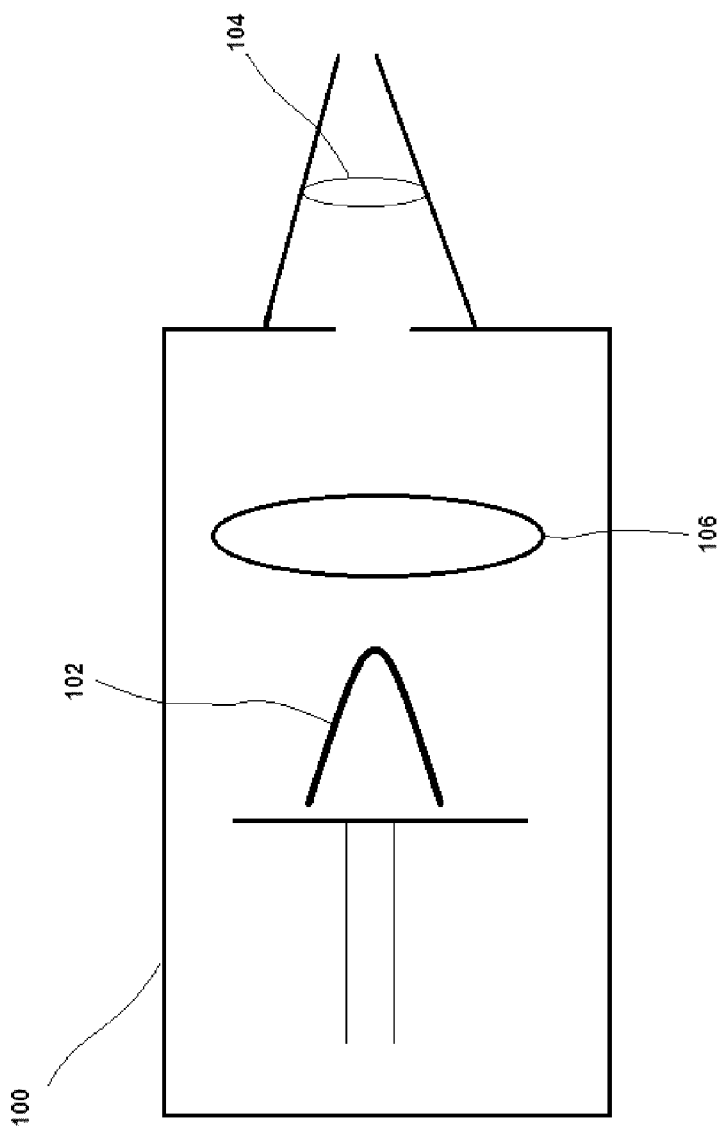
FIG. 4 depicts a schematic plan view of one embodiment of the light source.

The light source device 100 itself can be an incandescent bulb, a laser, or a light emitting diode 102, as well as other light sources known in the art. A device generating a focused beam of light 20 is preferred. A collimating lens 106 can improve the focus of the light beam 20. While a perfect polarizer 104 having an extinction coefficient of 1 would be ideal, in practice such polarizers 104 are not readily available. Using an admixture of both S and P polarization states prevents the reflectivity of the light waves 22 from going to zero, resulting in a larger signal for analysis with a corresponding relative minimization of signal noise, thus increasing sensitivity. In the most preferred embodiment of the present invention the light source 100 comprises a light emitting diode 102 producing a yellow light with a peak wavelength at 589 nm and a collimating lens 106, with the polarizer 104 positioned after the collimating lens 106. See FIG. 4.

The light detector 200 can be any device known in the art capable of measuring the intensity of light waves 22 directed thereon. Such devices include photodiodes, phototransistors, photo cells, cameras (such as ccd or CID) coupled to a computer, photomultiplier tubes, and the like, either amplified or unamplified. In the preferred embodiment the light detector 200 is a photodiode having an integrated operational amplifier. In an alternative embodiment of the present invention the light detector 200 comprises the polarizer 104. In yet another alternative embodiment of the present invention the light detector 200 further comprises a focusing lens.

The subject mount 300 component of the present invention secures the test subject 10 to the refractometer 1 in a specific orientation in relation to the light source 100 and light detector 200. Because the algorithm used for calculating the refractive index of the test subject 10 requires precise measurement of angles and light wave 22 intensity, it is critical that the angle between the light source 100 and the subject 10 and the angle between the subject 10 and the light detector 200 be known and substantially identical during all measurements. This is achieved in part by knowing the precise orientation of the test subject 10.

Figure 2:
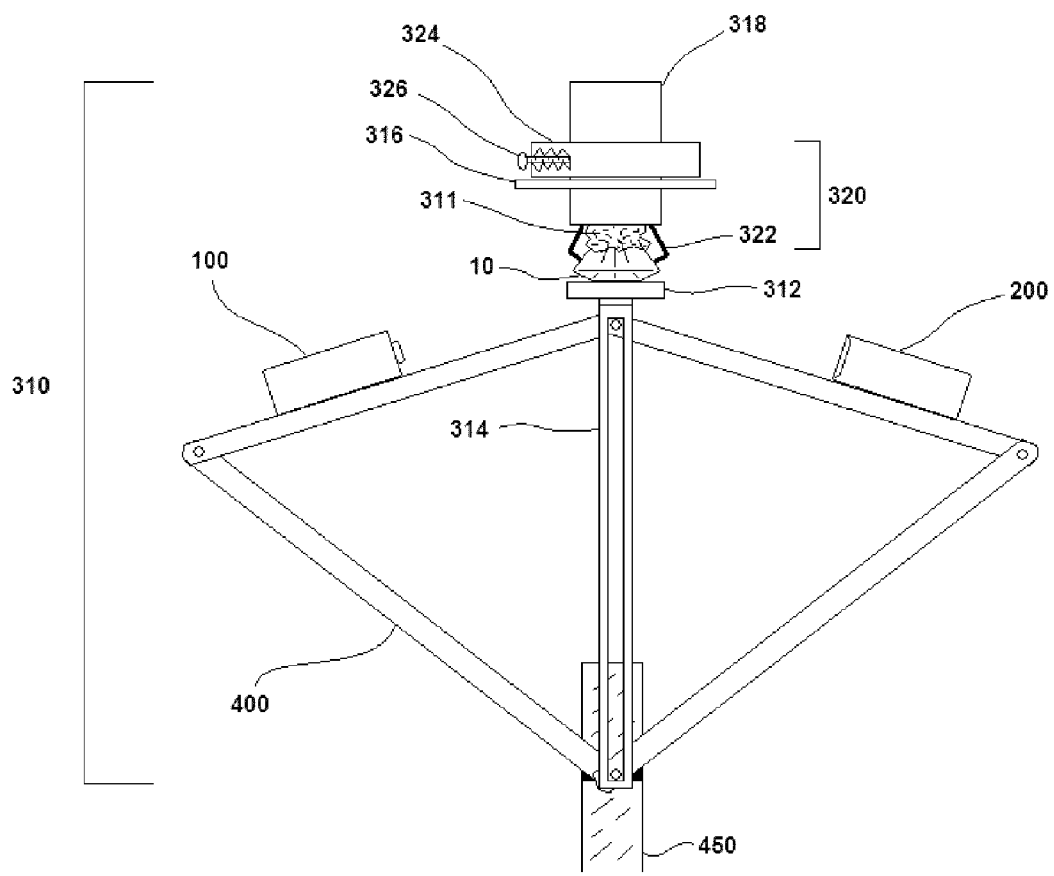
FIG. 2 depicts a detailed schematic plan view of one embodiment of the subject mount showing both orienting means (planar table member) and securing component.

In the preferred embodiment the subject mount 300 comprises an orienting means 310 and a securing component 320. See FIG. 2. The orienting means 310 is capable of positioning the subject 10 relative to the refractometer 1 in a specific and known orientation. As such it should itself be positionable. This can be achieved by a series of mechanical linkages, the use of ball joints, gears, movable arms, and the like. Alternatively, a malleable substance may be used to retain the subject 10. The test subject 10 is placed into the orienting means 310 and then manipulated until the subject 10 achieves its desired orientation.

To assist with the manipulation of the subject 10, in the preferred embodiment a multi-component subject mount 300 is used. See FIG. 2. In this embodiment the orienting means 310 comprises a substantially planar table member 312, oriented substantially horizontally, having a vertical support member 314 depending downward from the bottom of the planar table member 312. The vertical support member 314 has a milled out slot which slides over protrusions located at top pivot 442 and bottom pivot 448, thereby orienting the planar table member 312 at its desired position. When installed onto the refractometer 1, the planar table member 312 is intended to contact the subject 10. In this embodiment the orienting means 310 further comprises putty or wax 311 into which the subject 10 is pressed, such that the subject 10 can move within the putty or wax 311 to achieve correct orientation. The orienting means 310 further comprises a rod 318 and a guide 316. The guide 316 is fixedly attached to the main structure of the refractometer 1 in a substantially horizontal orientation. The rod 318 is suitably adapted to hold the putty or wax 311 onto its lower end. The rod 318 passes through a central aperture of the guide 316 and is retained therein, with the rod 318 and the aperture being suitably dimensioned to allow the rod 318 to move vertically within the aperture with a minimum of lateral movement. The securing component 320 of the subject mount 300 comprises a collar 324 having a set screw 326. The collar 324 is placed onto the rod 318 above the guide 316 with the set screw 326 in a loosened state. The rod 318 is adjusted vertically until it is in the desired position, then the set screw 326 is tightened, thereby securing the collar 324 onto the rod 318. Notwithstanding the collar 324 being locked onto the rod 318, the rod 318 may be moved vertically within the aperture of the guide 316. The securing component 320 may also comprise a lockable clamp 322 to secure the subject 10.

In this embodiment, the subject 10 is placed into the refractometer 1 and properly oriented by first placing the vertical support member 314 onto the refractometer 1. The test subject 10 is then pressed into the putty or wax 311 on the underside of the rod 318. After the subject 10 is placed into the putty or wax 311, the rod 318 is lowered towards the planar table member 312, which is located below the subject 10, until the subject 10 contacts the planar table member 312. Preferably the subject 10 comprises at least one substantially planar surface (such as a facet of a gemstone) which is oriented downwards. The contact of the planar surface of the subject 10 with the planar table member 312 continues until the two surfaces are fully engaged, resulting in the subject 10 having at least one surface oriented substantially horizontally. The subject may then be locked into place by the clamp 322. The collar 324 is locked onto the rod 318 by the set screw 326 to secure the desired orientation of the subject 10, the rod 318 is lifted, separating the subject 10 from the planar table member 312, and the vertical support member 314 is removed from the refractometer 1. The rod 318 is then lowered onto the guide 316. Note that the rod 318 can rotate within the guide 316. This allows for more precise orientation of the subject 10.

The positioning device 400 of the present invention is critical to its proper operation. It must be capable of dynamically orienting the light source 100 and the light detector 200 in relation to the subject 10 when the subject 10 is mounted on the subject mount 300, whereby for all orientations of the light source 100 relative to the subject 10 the light detector 200 is oriented at substantially the same angle to the subject 10. This may be achieved through mechanical or optical means. For example, the light source 100 and the light detector 200 may be rotated about a perpendicular axis to the same (but opposite) degree, while simultaneously being raised or lowered in relation to the subject 10 (to ensure convergence of the light waves with the subject 10). The light source 100 and the light detector 200 may be mounted on the ends of pivoting armatures, which pivot to the same (but opposite) degree, while simultaneously being raised or lowered in relation to the subject 10. The light source 100 and the light detector 200 may be in fixed relation to the subject 10, but mirrors or prisms interposed between the light source 100 and subject 10 and between the subject 10 and light detector 200 may be used to redirect the light waves 20,22; the mirrors and/or prisms would be mechanically positioned to mimic the physical positioning of the light source 100 and light detector 200 in relation to the subject 10, as described above.

Figure 3A:
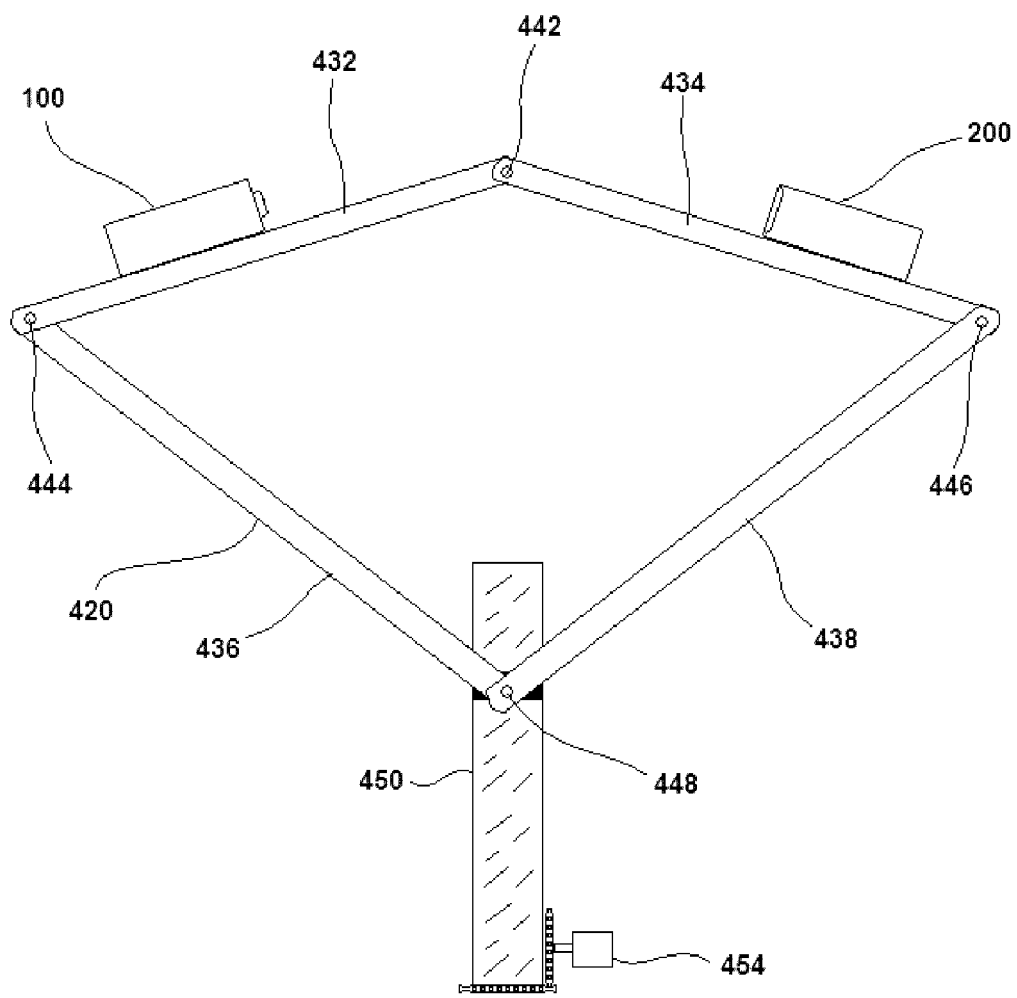
FIG. 3A depicts a detailed schematic plan view of one embodiment of the positioning means (pantograph).

In the preferred embodiment, the positioning device 400 comprises a pantograph 420. See FIG. 3A. The pantograph 420 has an upper left arm 432, an upper right arm 434, a lower left arm 436, and a lower right arm 438. The upper left arm 432 and the upper right arm 434 of the pantograph 420 are of substantially the same length. The lower left arm 436 and the lower right arm 438 of the pantograph 420 are also of substantially the same length. The first end of the upper left arm 432 is pivotally connected to the first end of the upper right arm 434 at a top pivot 442. The second end of the upper left arm 432 is pivotally connected to the second end of the lower left arm 436 at a left pivot 444. The second end of the upper right arm 434 is pivotally connected to the second end of the lower right arm 438 at a right pivot 446. The first end of the lower left arm 436 is pivotally connected to the first end of the lower right arm 438 at a bottom pivot 448. So structured, the pantograph 420 forms a diamond shape where each of the arms can change its orientation to each other arm.

Figure 3B:
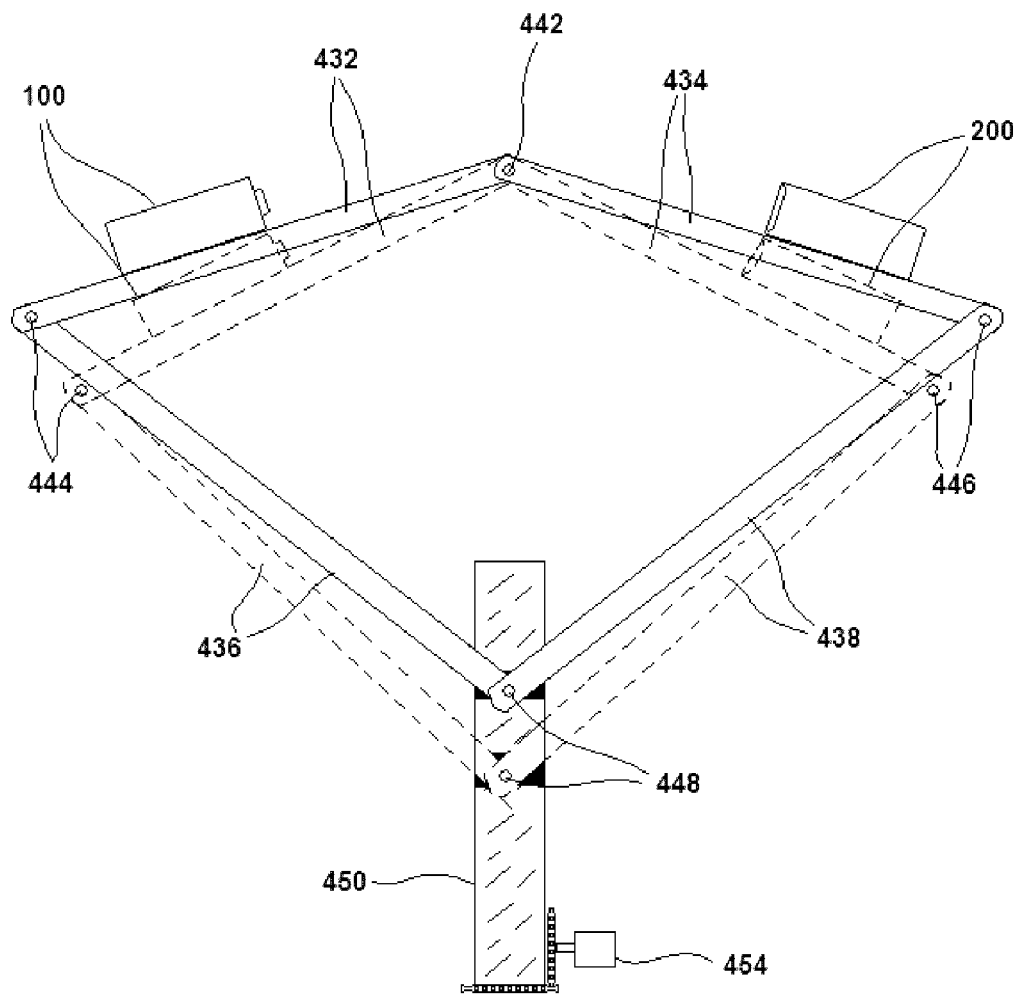
FIG. 3B depicts a detailed schematic plan view of the embodiment of the positioning means in FIG. 3A shown in a first position and in a second position (in ghost lines).

The top pivot 442 of the pantograph 420 is in fixed relation to the refractometer 1. The other three pivots 444,446,448 are in movable relation to the refractometer 1. The pantograph 420 is located below the subject 10 with the top pivot 442 positioned below the subject mount 300 along a vertical axis to the subject mount 300. A vertical positioner 450 is in connection with the bottom pivot 448 of the pantograph 420, positioned directly below the top pivot 442 along a vertical axis to the top pivot 442. The vertical positioner 450 moves the bottom pivot 448 upward and downward. So configured, an upward movement of the bottom pivot 448 by the vertical positioner 450 effects a simultaneous upward movement of the left and right pivots 444,446 to the same degree, thereby changing the angle of the upper left arm 432 relative to the subject 10 to the same degree as the angle of the upper right arm 434 relative to the subject 10, the angles becoming more acute relative to the subject 10. Similarly, a downward movement of the bottom pivot 448 by the vertical positioner 450 effects a simultaneous downward movement of the left and right pivots 444,446 to the same degree, thereby changing the angle of the upper left arm 432 relative to the subject 10 to the same degree as the angle of the upper right arm 434 relative to the subject 10, the angles becoming less acute relative to the subject 10. See FIG. 3B.

The light source 100 is mounted onto one of the upper arms 432,434 of the pantograph 420 such that it can direct light waves 20 onto the subject 10. The light detector 200 is mounted onto the other of the upper arms 434,432 such that it can receive light waves 22 reflected from the subject 10. Movement of the vertical positioner 450 as described above allows simultaneous re-orientation of the light source 100 and light detector 200 to the subject 10 at identical angles to the subject 10.

In one embodiment of the present invention the vertical positioner 450 comprises a worm gear. The worm gear is in connection with the bottom pivot 448 of the pantograph 420. Rotation of the worm gear in one direction raises the bottom pivot 448 and rotation of the worm gear in the opposite direction lowers the bottom pivot 448. In the preferred embodiment the vertical positioner 450 comprises an electric motor 454 to effect the upward and downward movement of the bottom pivot 448, with the motor 454 controlled by a digital computing device. Alternate embodiments of the vertical positioner 450 may comprise other suitable technologies, such as rack and pinion gearing, hydraulic lifters, or any other suitable mechanism for effecting vertical movement of the bottom pivot 448.

Figure 5:
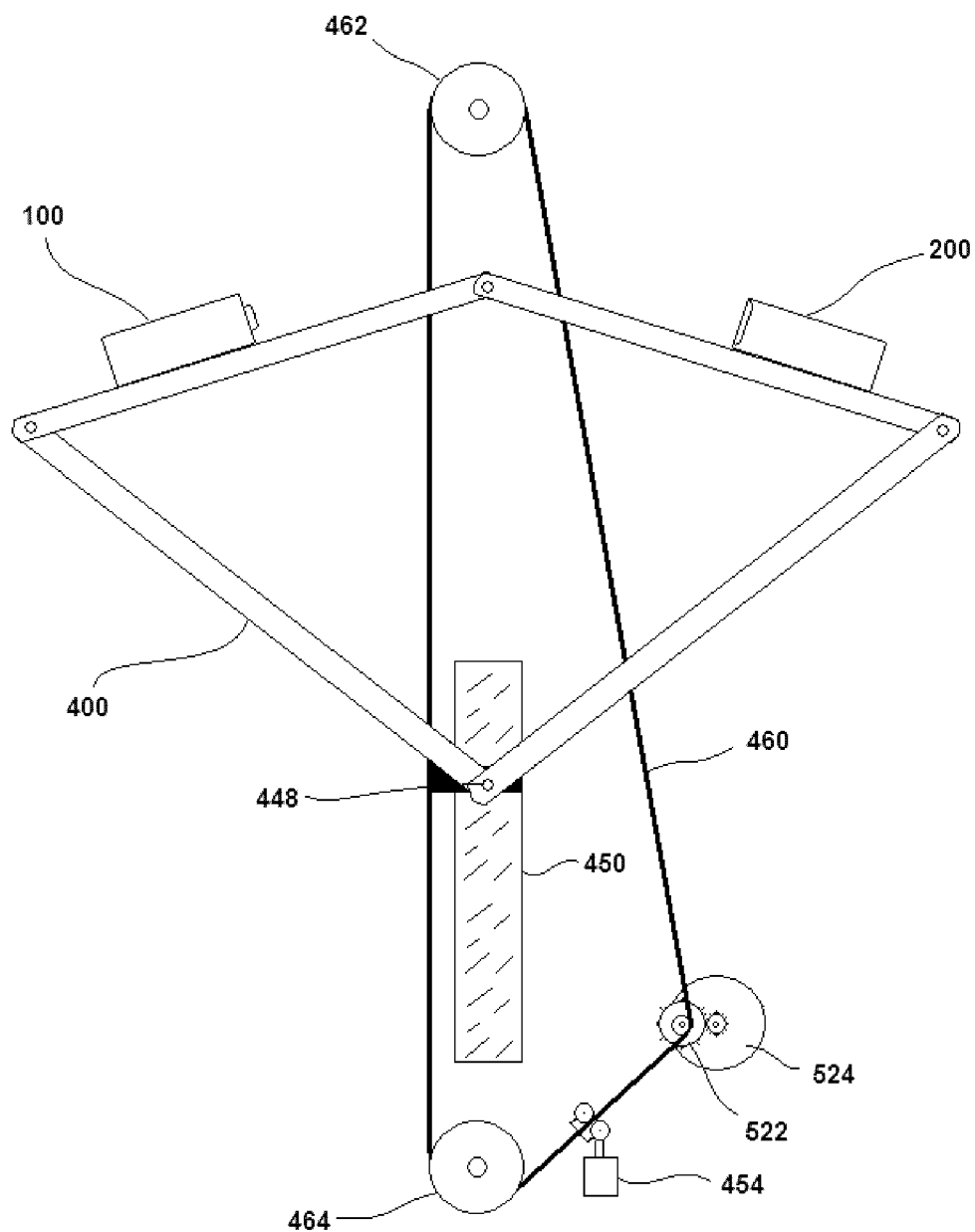
FIG. 5 depicts a detailed schematic plan view of one embodiment of the positioning means.

In the preferred embodiment of the present invention the vertical positioner 450 further comprises drive belt 460 disposed over a pair of fixed pulleys 462,464. See FIG. 5. The drive belt 460, which may be driven by the electric motor 454 controlled by a digital computing device, is in connection with the vertical positioner 450 and suitably adapted to move the vertical positioner 450 either upward or downward, effecting movement of the bottom pivot 448. Movement of the drive belt 460 in one direction raises the bottom pivot 448 and rotation of the drive belt 460 in the opposite direction lowers the bottom pivot 448. The drive belt 460 is further in connection with a rotary potentiometer 524.

The data gathering device 500 of the present invention measures the angle of the light source 100 and light detector 200 to the subject 10 and the intensity of light waves 22 directed onto the light detector 200. These measurements are taken over multiple data points, incorporating multiple angles. In the preferred embodiment the data gathering device 500 comprises a digital computing device, an angle measurement device 520, a first data connection 532 between the angle measurement device 520 and the digital computing device, and a second data connection 534 between the light detector 200 and the digital computing device. Data provided by the angle measurement device 520 regarding the angle of the light source 100 and light detector 200 to the subject 10 is communicated to the digital computing device by the first data connection 532. Data regarding the intensity of light waves 22 directed onto the light detector 200 is communicated to the digital computing device by the second data connection 534. The data connections 532,534 may be any applicable structure known in the art; at their simplest they may be simply wired connections between components.

The angle measurement device 520 may be any device that can accurately determine the angle of the light source 100 and the light detector 200 to the subject 10 normal. It may comprise computer software run on the digital computing device used to control the vertical positioner 450 of the pantograph 420; whereby the amount of movement of the vertical positioner 450 is translated into the change of the angle of the upper arms 432,434 of the pantograph 420. In such case the digital computing device of the data gathering device 500 may be the same digital computing device used to control the vertical positioner 450.

In another embodiment the angle measurement device 520 of the data gathering device 500 comprises one or more gears 522 in connection with the vertical positioner 450, a rotary potentiometer 524 in connection with the one or more gears 522, and a power source in connection with the potentiometer 524. The potentiometer 524 is in turn configured as a voltage divider circuit where the output voltage ranges from a minimal value (for example, 0 volts) at one extreme of resistance up to the maximum voltage (for example, 5 volts) at maximum resistance. Rotation of the potentiometer varies the resistance across this range. Movement of the vertical positioner 450 causes rotation of the one or more gears 522 which in turn causes rotation of the potentiometer 524. Measurement of the voltage by the digital computing device allows for a determination of the amount of rotation of the potentiometer 524. Because the gear ratio of the one or more gears 522 is known, the amount of vertical movement of the vertical positioner 450 can be calculated from the rotation of the potentiometer 524, and ultimately the angle of the light source 100 and the light detector 200 to the subject 10 normal can be determined from this movement. (Where the vertical positioner 450 is in connection with a pantograph 420 having all four arms 432,434,436,438 of substantially the same length, the angle theta to the subject 10 normal is calculated as arccos(D/2*L), where L is the length of an arm of the pantograph 420 and D is the vertical distance between the top pivot 442 and the bottom pivot 448 of the pantograph 420. A calibration procedure determines how the resistance of the potentiometer 524 relates to D so that measuring the voltage from the potentiometer 524 allows calculation of resistance and a determination of D.) Other embodiments of the angle measurement device 520 are also contemplated by the present invention.

Figure 6:
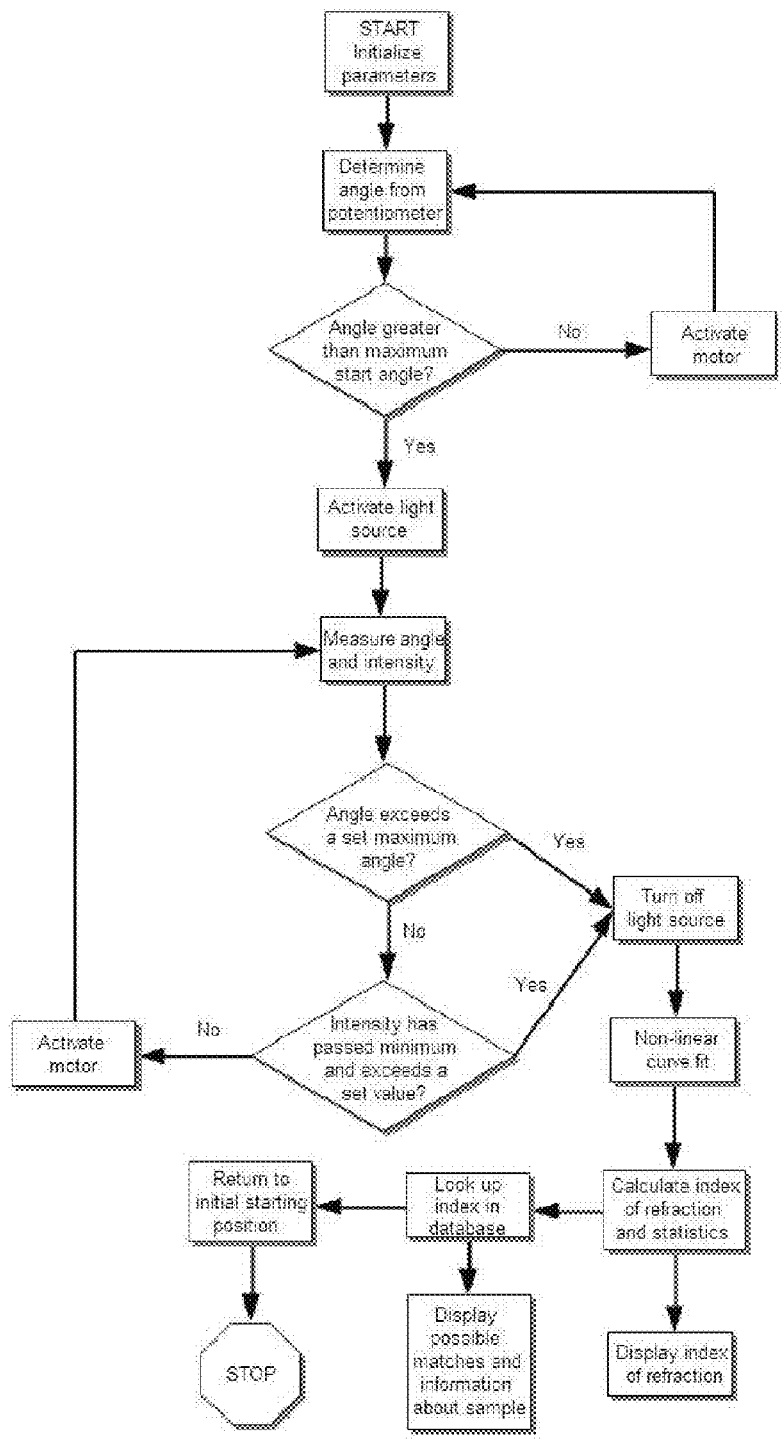
FIG. 6 depicts a flow chart detailing the computational analysis performed by the computational device.

The computational device 600 of the present invention uses an algorithm to analyze input data received from the data gathering device 500 to calculate a numeric value representing the refractive index of the subject 10. The data is preferably gathered by the data gathering device 500 over multiple angles of orientation of the light source 100 and light detector 200 to the subject 10. See FIG. 6. In one embodiment the computational device 600 comprises a digital computing device. The digital computing device must be in connection with the data gathering device 500. The digital computing device of the computational device 600 may also be the same digital computing device used by the data gathering device 500 and/or the angle measurement device 520 and/or the positioning device 400.

The digital computing device of the computational device 600 must have a user interface permitting the input and output of data, and it must be capable of running one or more computer software programs. The computer software programs must embody at least one algorithm for calculating the refractive index of the test subject 10 based on data including at least the angle of the light source 100 and light detector 200 to the subject 10 and for each such angle the intensity of light waves 22 directed onto the light detector 200. In the preferred embodiment the data will include multiple data sets representing multiple associations of angles and light intensity.

Specifically, each data set comprises an angle and a corresponding measurement of reflected light 22 intensity. The angle is determined from the angle measurement device 520 and the intensity is determined from the light detector 200. Once a data set is obtained, the positioning device 400 changes the angle and a new data set is obtained. This process is repeated until a predetermined condition arises, such as an optimum number of data sets is retrieved or the full range of angles has been measured or a certain intensity reading is found. Upon completing the data gathering process the computational device 600 analyzes the reflectivity data as a function of the angle using nonlinear curve fitting, which extracts the index of refraction. The calculated measured refractive index is displayed to the user. In one alternative embodiment, the calculated measured refractive index is further compared against data stored in a database and an identification of the test subject 10 is returned upon best match analysis. Software may be used to look up matches in the database taking into account the measured refractive index and the uncertainty as well as the known range that materials fall into. The software produces best matches and may further provide the user with pictures (macroscopic and microscopic), details about the subject 10, and further information that might help identify the subject 10 (including a description of the appearance of the substance as well as material properties such as hardness and specific gravity). The software may also generate a graphic representation of the resulting curve of light intensity versus incident angle, the shape of which can be analyzed by the user to determine the quality of the measurement.

To insure the greatest range of calculated refractive indices, the positioning device 400 should be able to establish angles at least in the range of 40 degrees to 75 degrees to the normal. This range allows measurement of refractive indices from less than 1.333 to greater than 3.000. Because the computer software uses multiple data sets, in applying the Fresnel Equations to reflected intensity as a function of angle a more accurate result is achieved. Nonlinear curve fitting is used to extract the index of refraction from the data set. Curve fitting of the entire data set allows consideration of both P-polarization and S-polarization states, providing multiple advantages: imperfect polarizers 104 (e.g., those with extinction coefficients less than 1) and imperfect alignment no longer contribute fundamental error in determining the refractive index; the admixture of both P-polarization and S-polarization states means the reflectivity will not go to zero, thus maintaining a relatively large signal compared to relatively small noise; and a combination of P-polarization and S-polarization changes the functional form of the reflectivity as a function of angle so that the curvature in the vicinity of the minimum decreases, thus making measurements extremely close the minimum less critical. These advantages provide significant improvement over prior art devices which depend on a single data set and visual observation of minimum light intensity.

The present invention also contemplates a method of determining the identity of an unknown substance using its calculated refractive index. The method comprises the following steps:

A. obtain a refractometer 1 configured as described above;
B. place the test substance into the refractometer 1;
C. orient the substance relative to the light source 100 and light detector 200 and secure it in said orientation to the subject mount 300;
D. activate the light source 100;
E. activate the positioning device 400 to dynamically orient the light source 100 and the light detector 200 through a series of angles in relation to the substance, with the light source 100 and the light detector 200 being simultaneously oriented at substantially the same angle to the substance, and for each such angle:
   E1. measure the angle of the light source 100 and the light detector 200 relative to the substance via the data gathering device 500, and
   E2. measure the intensity of light waves 22 directed onto the light detector 200 via the data gathering device 500;
F. provide data retrieved in substeps E1 and E2 to the computational device 600;
G. use the computational device 600 to perform an algorithm to determine the refractive index of the substance from the data retrieved in substeps E1 and E2; and H. compare the refractive index calculated in step G against known values of refractive indices of known substances to determine the identity of the test substance.

What has been described and illustrated herein is a preferred embodiment of the invention along with some it its variations. The terms, descriptions and figures used herein are set forth by way of illustration only and are not meant as limitations. Those skilled in the art will recognize that many variations are possible within the spirit and scope of the invention as defined in the following claims in which all terms are meant in their broadest, reasonable sense unless otherwise indicated.

We claim:

1. A refractometer comprising
   a light source, said light source capable of emitting a known spectrum of light waves at a substantially constant intensity and directing said light waves at a test subject;
   a light detector, said light detector capable of recording the intensity of light waves directed thereon;
   a polarizer, said polarizer suitably positioned to act upon said light waves;
   a subject mount, said mount capable of securing a test subject to the refractometer in a specific orientation in relation to the light source and light detector;
   a positioning device, said positioning device capable of dynamically orienting the light source and the light detector in relation to the subject when the subject is mounted on the subject mount, whereby for all orientations of the light source relative to the subject the light detector is oriented at substantially the same angle to the subject;
   a data gathering device, said data gathering device capable of measuring the angle of the light source and light detector to the subject and the intensity of light waves directed onto the light detector; and
   a computational device, said computational device using an algorithm to analyze input data from the data gathering device to calculate a numeric value representing the refractive index of the subject;
   whereby data is gathered by the data gathering device over multiple angles of orientation of the light source and light detector to the subject.

2. The refractometer of claim 1 wherein the light source is one of the group of: light emitting diode, laser, and incandescent bulb.

3. The refractometer of claim 1 wherein the light source is a yellow light emitting diode capable of emitting light waves falling within the range of 550 nm to 600 nm.

4. The refractometer of claim 1 wherein the polarizer is integrated with the light source.

5. The refractometer of claim 1 wherein the light source comprises a collimating lens.

6. The refractometer of claim 4 wherein the light source further comprises
   a light emitting diode; and
   a collimating lens.

7. The refractometer of claim 1 wherein the light detector is one of the group of: photodiode, phototransistor, and photo cell.

8. The refractometer of claim 7 wherein the light detector further comprises an integrated amplifier.

9. The refractometer of claim 1 wherein the polarizer is integrated with the light detector.

10. The refractometer of claim 1 wherein the subject mount comprises
    an orienting means and a securing component;
    whereby the orienting means is capable of positioning the subject relative to the refractometer in a specific orientation and the securing component is capable of securing the subject to the refractometer once the desired orientation is achieved.

11. The refractometer of claim 10 wherein the orienting means of the subject mount further comprises a substantially planar table member oriented substantially horizontally, said planar table member capable of being moved in an upward and in a downward direction;
    wherein the subject is oriented by the orienting means by the planar table member being raised until it contacts the subject causing a surface of the subject to fully align with the planar table member, thereby orienting said surface substantially horizontally.

12. The refractometer of claim 11 wherein the orienting means comprises one of the group of: putty and wax.

13. The refractometer of claim 10 wherein the securing component of the subject mount comprises a lockable clamp suitably adapted to retain the subject in a fixed orientation relative to the refractometer.

14. The refractometer of claim 1 wherein the positioning device comprises
    a pantograph, with the pantograph having an upper left arm, an upper right arm, a lower left arm, and a lower right arm, with the upper left and upper right arms being of substantially the same length and the lower left and lower right arms being of substantially the same length, with each of the arms having a first and second end,
    with the first end of the upper left arm pivotally connected to the first end of the upper right arm at a top pivot, the second end of the upper left arm pivotally connected to the second end of the lower left arm at a left pivot, the second end of the upper right arm pivotally connected to the second end of the lower right arm at a right pivot, and the first end of the lower left arm pivotally connected to the first end of the lower right arm at a bottom pivot,
    with the top pivot in fixed relation to the refractometer and the other three pivots in movable relation to the refractometer,
    with the pantograph located below the subject with the top pivot positioned below the subject mount along a vertical axis to the subject mount, and
    with the light source mounted onto one of either the upper left arm and the upper right arm and the light detector mounted onto the other of the upper left arm and the upper right arm; and
    a vertical positioner, said vertical positioner positioned directly below the top pivot along a vertical axis to the top pivot, said vertical positioner in connection with the bottom pivot, said vertical positioner capable of moving the bottom pivot upward and downward;
    whereby an upward movement of the bottom pivot by the vertical positioner effects an upward movement of the left pivot and an upward movement of the right pivot to the same degree, thereby changing the angle of the upper left arm relative to the subject to the same degree as the angle of the upper right arm relative to the subject, said angles becoming more acute relative to the subject, and
    a downward movement of the bottom pivot by the vertical positioner effects a downward movement of the left pivot and a downward movement of the right pivot to the same degree, thereby changing the angle of the upper left arm relative to the subject to the same degree as the angle of the upper right arm relative to the subject, said angles becoming less acute relative to the subject, whereby movement of the vertical positioner allows simultaneous re-orientation of the light source and light detector relative to the subject at identical angles to the subject.

15. The refractometer of claim 14 wherein the vertical positioner comprises an electric motor to effect the upward and downward movement of the bottom pivot.

16. The refractometer of claim 1 wherein the positioning device is controlled by a digital computing device.

17. The refractometer of claim 1 wherein the data gathering device comprises
a digital computing device,
an angle measurement device,
a first data connection between the angle measurement device and the digital computing device, and
a second data connection between the light detector and the digital computing device;
whereby data provided by the angle measurement device regarding the angle of the light source and light detector to the subject is communicated to the digital computing device by the first data connection, and data regarding the intensity of light waves directed onto the light detector is communicated to the digital computing device by the second data connection.

18. The refractometer of claim 17 wherein the angle measurement device of the data gathering device comprises
one or more gears in connection with the pantograph,
a rotary potentiometer in connection with the one or more gears, and
a power source in connection with the potentiometer;
whereby movement of the pantograph causes rotation of the one or more gears which in turn causes movement of the potentiometer, changing the voltage across the potentiometer to a measurable degree correlating to the change of the angle of the upper arms of the pantograph relative to the subject.

19. The refractometer of claim 1 wherein the computational device comprises
a digital computing device, said digital computing device being in connection with the data gathering device, said digital computing device having a user interface permitting the input and output of data, and said digital computing device being capable of running one or more computer software programs;
wherein said one or more computer software programs embody at least one algorithm for calculating the refractive index of the test subject based on multiple data sets, each said data set including at least the angle of the light source and light detector to the subject and the intensity of light waves directed onto the light detector.

20. The refractometer of claim 19 wherein the computational device further comprises
a database, said database containing an identification of substances by their respective refractive indices; and
one or more computer software programs capable of comparing the calculated refractive index of the test subject against information contained in the database to determine a best match identification of the test subject.

21. A method of determining the identity of a substance comprising the following steps:
A. obtaining a refractometer, said refractometer comprising
a light source, said light source capable of emitting a known spectrum of light waves at a substantially constant intensity and directing said light waves at a test subject;
a light detector, said light detector capable of recording the intensity of light waves directed thereon;
a polarizer, said polarizer suitably positioned to act upon said light waves;
a subject mount, said mount capable of securing the test substance to the refractometer in a specific orientation in relation to the light source and light detector;
a positioning device, said positioning device capable of dynamically orienting the light source and the light detector in relation to the test substance when the substance is mounted on the subject mount, whereby for all orientations of the light source the light detector is oriented at substantially the same angle to the substance;
a data gathering device, said data gathering device capable of measuring the angle of the light source and light detector to the subject and the intensity of light waves directed onto the light detector; and
a computational device, said computational device using an algorithm to analyze input data from the data gathering device to calculate a numeric value representing the refractive index of the subject;
whereby data is gathered by the data gathering device over multiple angles of orientation of the light source and light detector to the subject;
B. placing the test substance into the refractometer;
C. orienting the substance relative to the light source and light detector and securing it in said orientation to the subject mount;
D. activating the light source;
E. activating the positioning device to dynamically orient the light source and the light detector through a series of angles in relation to the substance, with the light source and the light detector being simultaneously oriented at substantially the same angle to the substance, and for each such angle:
E1. measuring the angle of the light source and the light detector relative to the substance with the data gathering device, and
E2. measuring the intensity of light waves directed onto the light detector with the data gathering device;
F. providing data retrieved in substeps E1 and E2 to the computational device;
G. using the computational device to perform an algorithm to determine the refractive index of the substance from the data retrieved in substeps E1 and E2; and
H. comparing the refractive index calculated in step G against known values of refractive indices of known substances to determine the identity of the test substance.

* * * * *